United States Patent [19]

Ooishi

[11] Patent Number: 4,612,307

[45] Date of Patent: Sep. 16, 1986

[54] CONTROLLING AGENT FOR WOOD ROTTING FUNGI

[75] Inventor: Tadashi Ooishi, Toyonaka, Japan

[73] Assignee: Sumitomo Chemical Company, Limited, Osaka, Japan

[21] Appl. No.: 800,092

[22] Filed: Nov. 20, 1985

Related U.S. Application Data

[63] Continuation of Ser. No. 658,630, Oct. 9, 1984, abandoned.

[30] Foreign Application Priority Data

Oct. 21, 1983 [JP] Japan ................................ 58-198152

[51] Int. Cl.⁴ ............................................. A01N 57/10
[52] U.S. Cl. ..................................................... 514/147
[58] Field of Search ......................................... 514/147

[56] References Cited

U.S. PATENT DOCUMENTS 4,039,635 8/1977 Kato et al. ........................... 260/954
4,304,587 12/1981 Cummings .......................... 514/147

FOREIGN PATENT DOCUMENTS 47-15717 5/1972 Japan .................................. 514/147

OTHER PUBLICATIONS

Chemical Abstracts, vol. 98, No. 17, Apr. 25, 1983, p. 188, No. 138881t, Ohtsuki et al.
Chemical Abstracts, vol. 99, No. 11, Sep. 12, 1983, pp. 185–186, No. 83607w, Kato.

Primary Examiner—Albert T. Meyers
Assistant Examiner—John M. Kilcoyne
Attorney, Agent, or Firm—Stevens, Davis, Miller & Mosher

[57] ABSTRACT

The present invention relates to wood rotting fungicidal compositions comprising tolclofos-methyl as an active ingredient.

1 Claim, No Drawings

CONTROLLING AGENT FOR WOOD ROTTING FUNGI

This application is a continuation of application Ser. No. 658,630, filed Oct. 9, 1984, now abandoned.

The present invention relates to wood rotting fungicidal compositions comprising tolclofos-methyl[O,O-dimethyl O-(2,6-dichloro-4-methylphenyl)phosphorothioate] as an active ingredient.

Recently, a high degree of heat insulation is being introduced into wooden houses for the purpose of energy saving. The use of heat insulating materials to floors, walls, etc. surely makes the wooden houses comfortable to live in, but it brings dew condensation and subsequent high humidity as well as poor ventilation to the portions. The portions, therefore, become the most suitable place for wood rotting fungi to work actively in. These fungi propagate by decomposing celluloses which are components of woods and taking nutritive substances from the decomposed product, so that they markedly lower the strength of woods and particularly a great damage of woods causes the collapse of houses. Such damage can be lightened to some degree by house-building methods, but for obtaining a more sufficient effect, it becomes necessary to apply chemicals having an antimicrobial activity on wood rotting fungi themselves.

In the present situation like this, the present inventor endeavored to develop a controlling agent for wood rotting fungi, and as a result, found that tolclofos-methyl, as described as an agricultural and horticultural soil fungicide in U.S. Pat. No. 4,039,635, has excellent controlling effect on wood rotting fungi such as *Tyromyces palustris, Serpula lacrymans, Coriolus versicolar,* etc., and besides that these wood rotting fungi can be controlled and the damage of woods by these rotting fungi such as lowering in strength, etc. can be lightened by applying tolclofos-methyl to the land wherein building of wooden houses, etc. is expected or to the soil surface below the floors after building. The present inventors thus completed the present invention.

When tolclofos-methyl is used in controlling wood rotting fungi, it may be used as such without adding any other component, but generally, it is formulated into wettable powders, granules, dusts, etc. by mixing with solid carriers, surface active agents and other auxiliaries for formulation. The preparations contain 0.1 to 99.9% by weight, preferably 0.2 to 80% by weight of the active ingredient.

The solid carrier described above includes for example the fine powders or granules of kaolin clay, attapulgite clay, bentonite, terra alba, pyrophyllite, talc, diatomaceous earth, calcite, corn stalk powder, walnut shell powder, urea, ammonium sulfate, synthetic hydrated silicon dioxide and the like. The surface active agent used for emulsification, dispersion, etc. includes for example anionic surface active agents such as the salt of alkyl sulfate, alkyl(aryl)sulfonates, dialkyl sulfosuccinates, the salt of the phosphoric acid ester of polyoxyethylene alkylaryl ether, naphthalenesulfonic acid formalin condensates, etc. and nonionic surface active agents such as polyoxyethylene alkyl ether, polyoxyethylene polyoxypropylene block copolymers, sorbitan fatty acid esters, polyoxyethylene sorbitan fatty acid esters, etc. The auxiliary for formulation includes for example lignosulfonates, alginates, polyvinyl alcohol, gum arabic, CMC (carboxymethyl cellulose), PAP (ispropyl acid phosphate) and the like.

Next, formulation examples will be shown. Parts in the examples are by weight.

FORMULATION EXAMPLE 1

10 Parts of tolclofos-methyl, 85.7 parts of kaolin clay, 4 parts of synthetic hydrated silicon dioxide and 0.3 part of PAP are thoroughly pulverized and mixed to obtain a dust.

FORMULATION EXAMPLE 2

20 Parts of tolclofos-methyl, 5 parts of synthetic hydrated silicon dioxide, 5 parts of calcium lignosulfonate, 30 parts of bentonite and 40 parts of kaolin clay are thoroughly pulverized and mixed, well kneaded with water, granulated and dried to obtain a granule.

FORMULATION EXAMPLE 3

50 Parts of tolclofos-methyl, 3 parts of calcium lignosulfate, 2 parts of sodium lauryl sulfate and 45 parts of synthetic hydrated silicon dioxide are thoroughly pulverized and mixed to obtain a wettable powder.

When the wood rotting fungi are controlled with these preparations, the preparations, either as such or as aqueous solution, are sprayed or scattered onto soil surface (as need arises, they are mixed with the soil after spraying or scattering), or the soil is drenched with them. The granule, dust, etc. are used as such without dilution, and the wettable powder, etc. are used in dilution with water so that their concentration is 5 to 0.0005%, preferably 0.5 to 0.005%.

Next, that tolclofos-methyl is useful in controlling the wood rotting fungi will be illustrated with reference to the following test examples.

TEST EXAMPLE 1

Antimicrobial Test

Tolclofos-methyl formulated into a wettable powder according to Formulation Example 3 was diluted with water to a prescribed concentration, a definite amount of the resulting aqueous solution was added to a dissolved potato medium, and the mixture was run into a Petri dish and solidified. Separately from this, the colonies of *Tyromyces palustris, Serpula lacrymans* and *Coriolus versicolar,* as obtained by previous culture in potato media, were each punched with a cork borer of 5 mm in diameter, and the above solidified medium was inoculated with each disc-inoculum thus prepared. The Petri dishes containing the media inoculated with *Tyromyces palustris* and *Coriolus versicolar,* respectively, were placed in a constant-temperature apparatus kept at $26°\pm2°$ C., and the Petri dish containing the medium inoculated with *Serpula lacrymans* was placed in a constant-temperature apparatus kept at $20°\pm2°$ C. At the point when the mycelia in the untreated plots extended to about 80% of the diameter of the Petri dish, the condition of growth of the mycelia in the treated plots was examined, and the percentage of mycelium growth inhibition (%) was obtained from the following equation:

$$\text{Percentage of mycelium growth inhibition (\%)} = \frac{\begin{bmatrix}\text{length of}\\\text{mycelium in}\\\text{untreated}\\\text{plot (mm)}\end{bmatrix} - \begin{bmatrix}\text{length of}\\\text{mycelium in}\\\text{treated}\\\text{plot (mm)}\end{bmatrix}}{\text{length of mycelium in untreated plot (mm)}} \times 100$$

The result is shown in Table 1.

TABLE 1

| Test compound | Concentration of active ingredient applied (ppm) | Percentage of mycelium growth inhibition (%) | | |
|---|---|---|---|---|
| | | *Tyromyces palustris* | *Serpula lacrymans* | *Coriolus versicolar* |
| Tolclofos-methyl | 100 | 100.0 | 100.0 | 100.0 |
| | 10 | 100.0 | 100.0 | 100.0 |
| | 1 | 86.7 | 93.3 | 80.0 |
| Inoculated and untreated plot | — | 0.0 | 0.0 | 0.0 |

TEST EXAMPLE 2

Controlling Test on *Serpula lacrymans*

A wooden powder containing cultured *Serpula lacrymans* was mixed with a sterilized soil, and the mixture was filled in a plastic vat [inner dimension: 25 cm × 32 cm × 12 cm (high)] to a level of about 8 cm. Tolclofos-methyl formulated into a wettable powder according to Formulation example 3 was diluted with water to a prescribed concentration, and the mixture was drenched with the resulting aqueous solution of an amount corresponding to 3 liters per m². Several wood pieces of Japanese red pine [20 mm × 40 mm × 5 mm (thick)] were placed on the soil surface, and the whole plastic vat was covered with a polyvinyl chloride film and placed in a constant-temperature apparatus kept at 20° ± 2° C. and at a relative humidity of not less than 70%. After six weeks, the wood pieces were taken out to examine the condition of growth of the colony, and the damage index was obtained based on the following standard.

| Damage index | Condition of growth of colony |
|---|---|
| 0 | No colony is noticed on the surface of wood pieces. |
| 0.5 | About 5% of the colony is noticed on the surface of wood pieces. |
| 1 | About 20% of the colony is noticed on the surface of wood pieces. |
| 2 | About 50% of the colony is noticed on the surface of wood pieces. |
| 4 | Not less than 60% of the colony is noticed on the surface of wood pieces. |

Next, the degree of damage (%) was obtained according to the following equation:

$$\text{Degree of damage (\%)} = \frac{\Sigma\left\{\begin{pmatrix}\text{damage}\\\text{index}\end{pmatrix} \times \begin{pmatrix}\text{number of examined}\\\text{wood pieces}\end{pmatrix}\right\}}{\begin{pmatrix}\text{number of examined}\\\text{wood pieces}\end{pmatrix} \times 4} \times 100$$

The result is shown in Table 2.

TABLE 2

| Test compound | Concentration of active ingredient applied (ppm) | Degree of damage (%) |
|---|---|---|
| Tolclofos-methyl | 1000 | 0.0 |
| | 500 | 0.0 |
| | 250 | 0.0 |
| Inoculated and untreated plot | — | 90.0 |
| Uninoculated and untreated plot | — | 0.0 |

What is claimed is:

1. A method for controlling *Serpula lacrymans* fungi which comprises contacting said fungi with a fungicidally effective amount of tolclofos-methyl.

* * * * *